United States Patent [19]

Dayal

[11] Patent Number: 5,660,175
[45] Date of Patent: Aug. 26, 1997

[54] ENDOTRACHEAL DEVICE

[76] Inventor: Bimal Dayal, 6159 Pebble Beach Ct., Canfield, Ohio 44406

[21] Appl. No.: 517,492

[22] Filed: Aug. 21, 1995

[51] Int. Cl.$^6$ .................................................. A61M 16/00
[52] U.S. Cl. .................. 128/207.15; 128/207.14; 128/911; 128/912; 128/200.26
[58] Field of Search .................. 128/207.14, 207.15, 128/911, 912, 200.26

[56] References Cited

U.S. PATENT DOCUMENTS

| | | |
|---|---|---|
| 3,504,676 | 4/1970 | Lomholt .............................. 128/207.15 |
| 4,022,219 | 5/1977 | Basta . |
| 4,036,210 | 7/1977 | Campbell et al. . |
| 4,166,468 | 9/1979 | Maynie .............................. 128/207.15 |
| 4,214,593 | 7/1980 | Imbruce et al. . |
| 4,231,365 | 11/1980 | Scarberry . |
| 4,233,984 | 11/1980 | Walling . |
| 4,248,221 | 2/1981 | Winnard . |
| 4,344,436 | 8/1982 | Kubota . |
| 4,449,526 | 5/1984 | Elam .............................. 128/206.21 |
| 4,453,545 | 6/1984 | Inoue . |
| 4,840,172 | 6/1989 | Augustine et al. . |
| 4,850,371 | 7/1989 | Broadhurst et al. . |
| 5,033,466 | 7/1991 | Weymuller, Jr. . |
| 5,065,755 | 11/1991 | Klafta . |
| 5,253,643 | 10/1993 | Price . |
| 5,285,778 | 2/1994 | Mackin . |
| 5,309,906 | 5/1994 | LaBombard . |
| 5,315,992 | 5/1994 | Dalton .............................. 128/207.15 |
| 5,353,787 | 10/1994 | Price . |
| 5,372,131 | 12/1994 | Heinen .............................. 128/207.15 |

FOREIGN PATENT DOCUMENTS 439280  1/1975  U.S.S.R. .............................. 128/207.15

*Primary Examiner*—Vincent Millin
*Assistant Examiner*—William J. Deare, Jr.
*Attorney, Agent, or Firm*—Woodling, Krost & Rust

[57] ABSTRACT

The endotracheal device comprises a common slave unit and an endobronchial tube. The endobronchial tube is preformed for either left curvature or right curvature. The common slave unit includes a tracheal lumen and an endobronchial lumen. The endobronchial tube is inserted through the endobronchial lumen and into either the left or right bronchus. A first inflatable cuff secures the common slave unit with respect to the trachea. A second inflatable cuff secures the endobronchial tube with respect to the endobronchial lumen. A third inflatable cuff secures the endobronchial tube with respect to the bronchus of a human being

17 Claims, 10 Drawing Sheets

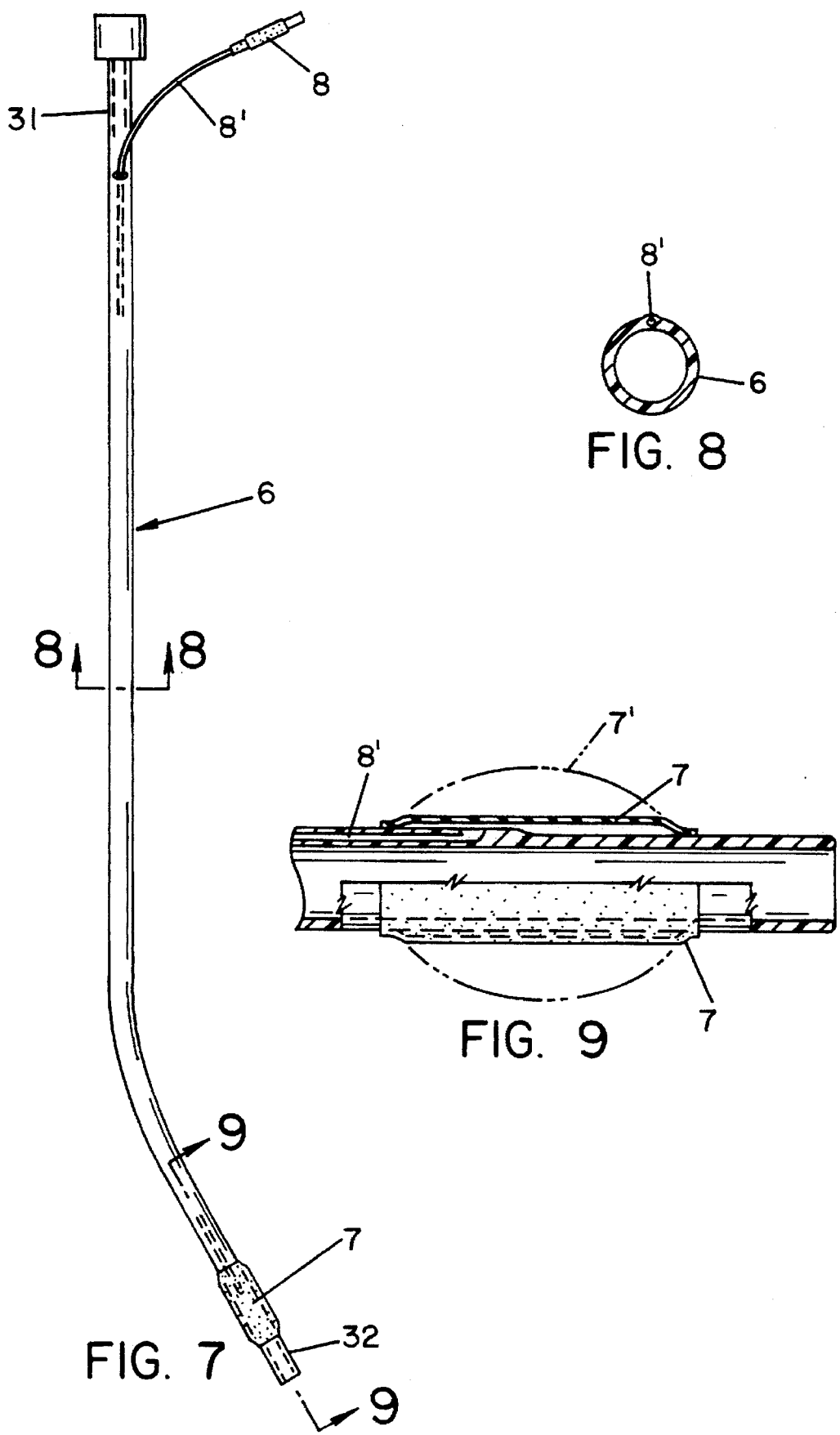

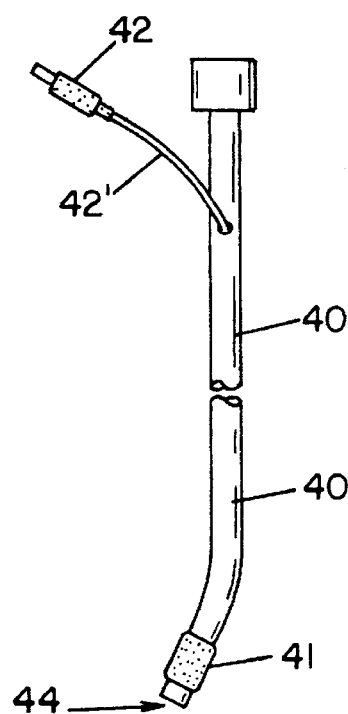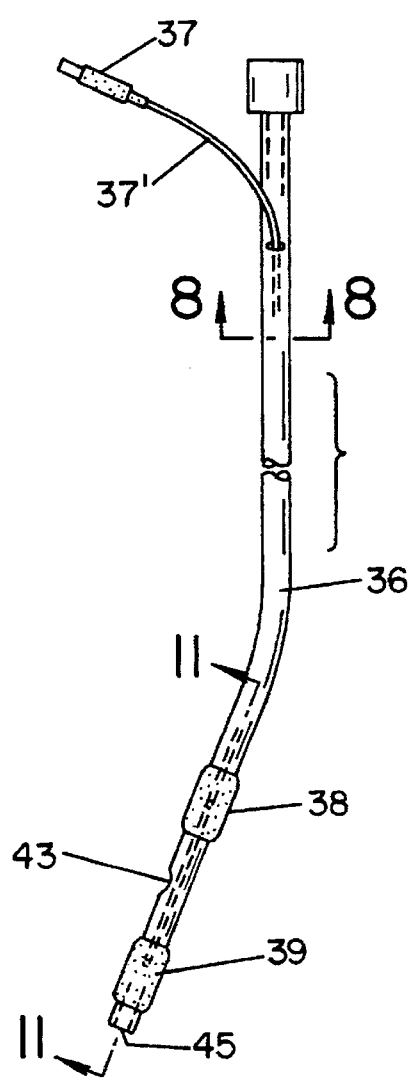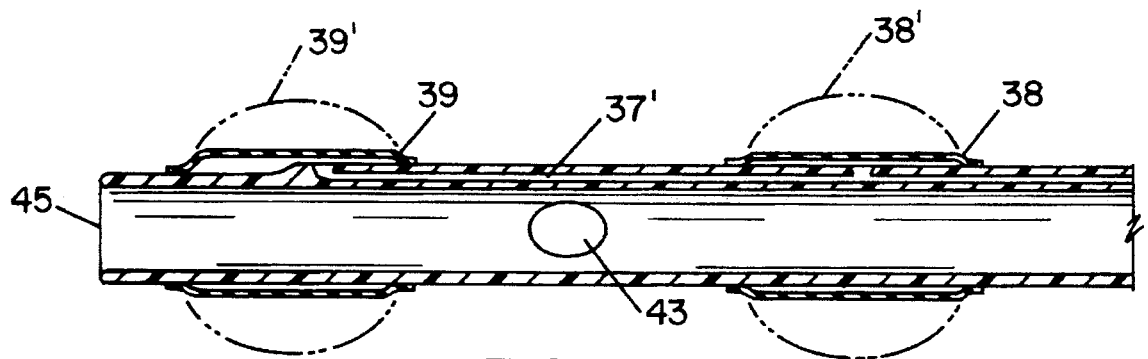
FIG. 10A
FIG. 10
FIG. 11

ENDOTRACHEAL DEVICE

FIELD OF THE INVENTION

This invention is in the field of a new endotracheal tube used to ventilate a single lung. The invention comprises two separate components. One component is a common slave unit and the other is an endobronchial unit. The invention provides single lung ventilation for surgical and non-surgical cases.

The present invention relates to a double lumen tube available in different sizes to be used in combination with endobronchial tubes which are also available in different sizes. The invention provides the ability to collapse a lung to undergo surgery thereon. The invention also provides ventilation of both lungs simultaneously if needed during surgery. The invention also provides for the easy placement of a common slave unit in the patient's trachea. The invention further allows the common slave unit to be left in place in the patient to provide post surgical ventilation.

BACKGROUND OF THE INVENTION

Single lung ventilation (intubation) and anesthesia have been practiced for many years. Single lung ventilation has been used for surgical and non-surgical procedures. Usually single lung ventilation is used during thoracic surgery.

Single lung ventilation is indicated when there is a need to prevent spillage of blood, pus, and/or infected material from a diseased lung to a healthy lung. Most thoracic surgeries are performed by placing the patient on his or her side. The disease lung is oriented such that it is on top of the healthy lung. This surgical position significantly increases the risk of contaminating the healthy lung with blood, pus, and/or other infected material by means of gravity from the diseased lung. Therefore effective isolation of the diseased lung is required.

Single lung ventilation is also indicated during the following surgical procedures: acute and chronic bronchial pulmonary fistula and removal of one lobe of a lung with sleeve resection.

Single lung ventilation and/or anesthesia is indicated when it is necessary to provide optimal surgical exposure. Optimal surgical exposure is achieved by not ventilating the diseased lung. This is also sometimes called "quiet" collapsed lung. This technique is used during lung resection, surgery on the esophagus and/or surgery on part of the aorta.

There are also non-surgical indications for use of single lung ventilation. For example, in certain intensive care treatments it is necessary to provide selective ventilation. Indication for such non-surgical single lung ventilation are acute respiratory failure and large chronic bronchopleural fistula.

There are several devices that are available for single lung ventilation. There is a class of devices called bronchial blockers which accomplish single lung ventilation. However, these devices are not satisfactory for all circumstances. The bronchial lockers have one common feature. They are all supplied with narrow lumen inflatable balloon tipped catheters which can be selectively placed in a desired lung. These narrow lumens are prone to blockage by blood, pus, etc. from the diseased lung. It is quite common during surgery that ventilation of the diseased lung is required. This cannot be done with narrow lumen bronchial blocker. The ventilation of a diseased lung when a narrow lumen bronchial blocker is used requires the deflation of the balloon cuff which secures the catheter in place. Once the endobronchial balloon cuff is deflated and/or repositioned an effective seal/isolation of the diseased lung is lost. This permits the spillage of blood, pus, and infected material to the healthy lung.

A second class of devices, single lumen endobronchial tubes, are known and used for single lung ventilation. These devices are used to isolate and ventilate one lung while surgery is performed on the other lung. These devices are supplied with two inflatable cuffs, a tracheal cuff and an endobronchial cuff. These devices are structurally simple but have major disadvantages. If and when it becomes necessary to inflate and ventilate the collapsed lung during anesthesia, the endobronchial tube has to be removed and repositioned subsequently. This allows a situation where blood, pus, and infected material may spill into the healthy lung. Additionally, when the ventilation has been accomplished, the endotracheal tube and cuffs need to be repositioned into the patient to complete administration of anesthesia. This is difficult during surgery when the patient is in the lateral position (i.e. on his side).

Additionally, when using single lumen endobronchial tubes to ventilate the right lung, it is extremely difficult to position the endobronchial tube and attendant cuff. Anatomically the distance between the bronchus supplying the right upper lobe and the tracheal bifurcation ms very short, usually 1.5 centimeters or less. This creates a situation where after placement of the endobronchial tube in the right main bronchus, either the outlet for the bronchus supplying the right upper lobe is occluded or the endobronchial tube goes beyond the outlet for the bronchus. This creates ventilation problems and does not permit the use of the entire right lung. This causes an increased incidence of hypoxia during surgery.

A third class of devices, double lumen endobronchial tubes, are known and used for single lung ventilation. The double lumen endobronchial tubes available are bulky and require considerable operator skills to properly position the tubes in the patient. The available double lumen endobronchial tubes have two narrow lumen tubes oriented side by side and two cuffs, an endobronchial cuff and a tracheal cuff.

U.S. Pat. No. 4,453,545 to Inoue discloses an endotracheal tube with a movable endobronchial blocker for one lung anesthesia. See, for example, FIG. 3-a of the '545 patent. Also, see FIG. 1-a of the '545 patent which illustrates a conventional single lumen endobronchial tube; and, see, FIG. 2 of the '545 patent which illustrates a conventional double lumen endobronchial tube. U.S. Pat. No. 4,453,545 to Inoue discloses at column 3, lines 10–35, the manner in which the Inoue invention is positioned in either lung.

The Inoue invention (U.S. Pat. No. 4,453,545) has the disadvantages of (1) being difficult to insert; and (2) it has a narrow, endobronchial lumen. Although the combined endobronchial tube and tracheal tube of Inoue (the '545 patent) as shown in FIG. 3-a thereof may be left in the patient if bilateral ventilation is required, Inoue is nonetheless disadvantaged by the difficulty of repositioning the endobronchial tube. The endobronchial tube of Inoue must be repositioned to increase the flow area during bilateral ventilation. Further, the endobronchial tube of Inoue is too narrow and is susceptible to blockages and the like.

SUMMARY OF THE INVENTION

It is an object of the present invention to provide an endotracheal device comprised of a common slave unit and an endobronchial tube.

It is an object of the present invention to provide a common slave unit which may reside in the patient post operatively.

It is an object of the present invention to provide a common slave unit which is easily installed into the patient. The common slave unit comprises an anterior tracheal passageway and a posterior endobronchial passageway shaped generally to correspond to the shape of a human glottis.

It is a further object of the invention to provide a common slave unit having a communicating passageway between the tracheal lumen and the endobronchial lumen.

It is a further object of the invention to provide an endobronchial tube which includes a preformed left curvature for insertion into the left main bronchus of a human being.

It is a further object of the invention to provide an endobronchial tube which includes a right preformed curvature for insertion into the right main bronchus of a human being.

It is a further object of the present invention to provide a common slave unit and an endobronchial tube which are flexible and easily insertable into a patient.

It is a further object of the present invention to provide a common slave unit and means for sealing and securing same with respect to the trachea of a human being. Additionally, it is an object of the invention to provide means for sealing and securing the endobronchial tube with respect to the endobronchial lumen of the common slave unit. Additionally, it is an object of the present invention to provide a sealing means for sealing the endobronchial tube with respect to the left or right main bronchus of a human being.

It is a further object of the present invention to provide a plurality of seals in the right bronchus of a human being so as to ensure the complete and full administration of anesthesia to the right lung.

It is a further object of the present invention to provide a communicating passageway between the tracheal lumen and the endobronchial lumen of the common slave unit.

It is a further object of the present invention to provide a common slave unit which individually or in combination with an endobronchial tube provides good ventilation.

Additional objects of the invention will be understood when taken in conjunction with the following Brief Description of the Drawings and Description of the Preferred Embodiment.

BRIEF DESCRIPTION OF THE DRAWINGS

FIG. 1 depicts the endobronchial tube 6 positioned in the left main bronchus 13. FIG. 1 generally shows the left and right bronchus of a human being.

FIG. 5 illustrates the second cuff 2 (inflated two prime) inflated 2' and the third cuff 3 (inflated three prime) inflated 3'. The tracheal lumen 1T and endobronchial lumen 1E are illustrated in FIG. 5.

FIG. 6 illustrates the tubular section 22 of the tracheal lumen 1T and the tubular section 23 of the endobronchial lumen 1E.

FIG. 7 illustrates a perspective view of the left endobronchial tube 6 preformed for left curvature for insertion into the left bronchus.

FIG. 8 is a cross-sectional view taken along the lines 8—8 of FIG. 7.

FIG. 9 is a cross-sectional view taken along the lines 9—9 of FIG. 7 illustrating the third inflatable cuff 7 and in its inflated state 7'. Also illustrated is the passageway 8' for inflating the third inflatable cuff 7.

FIG. 10A illustrates a perspective view of the right endobronchial tube preformed for right curvature for insertion into the right bronchus. FIG. 10A illustrates one inflatable cuff 41 located thereon.

FIG. 10 illustrates the preferred embodiment of the right endobronchial tube preformed for right curvature for positioning into the right bronchus. FIG. 10 illustrates two inflatable cuffs located thereon. This embodiment insures proper medication and ventilation for the right bronchus. Due to the anatomy of the right bronchus it is important that no occlusion of the upper bronchus occurs.

FIG. 11 illustrates a cross-sectional view taken along the lines 11—11 of FIG. 10. FIG. 11 illustrates two inflatable cuffs, 38 and 39, and an aperture 43.

FIG. 12C further illustrates the positioning of the endobronchial tube 6.

FIG. 12F further illustrates the inflation of the second inflatable cuff, sometimes referred to as the inner cuff.

FIG. 13A further illustrates the first inflatable cuff 2 in its inflated state. FIG. 13A further illustrates the endobronchial tube 36 preformed with right curvature as it is being inserted through the endobronchial lumen of he common slave unit.

FIG. 13D illustrates the inner cuff 3, the second inflatable cuff, inflated sealing and securing the endobronchial tube 36 with respect to the common slave unit.

DESCRIPTION OF THE PREFERRED EMBODIMENT

Figure 1:
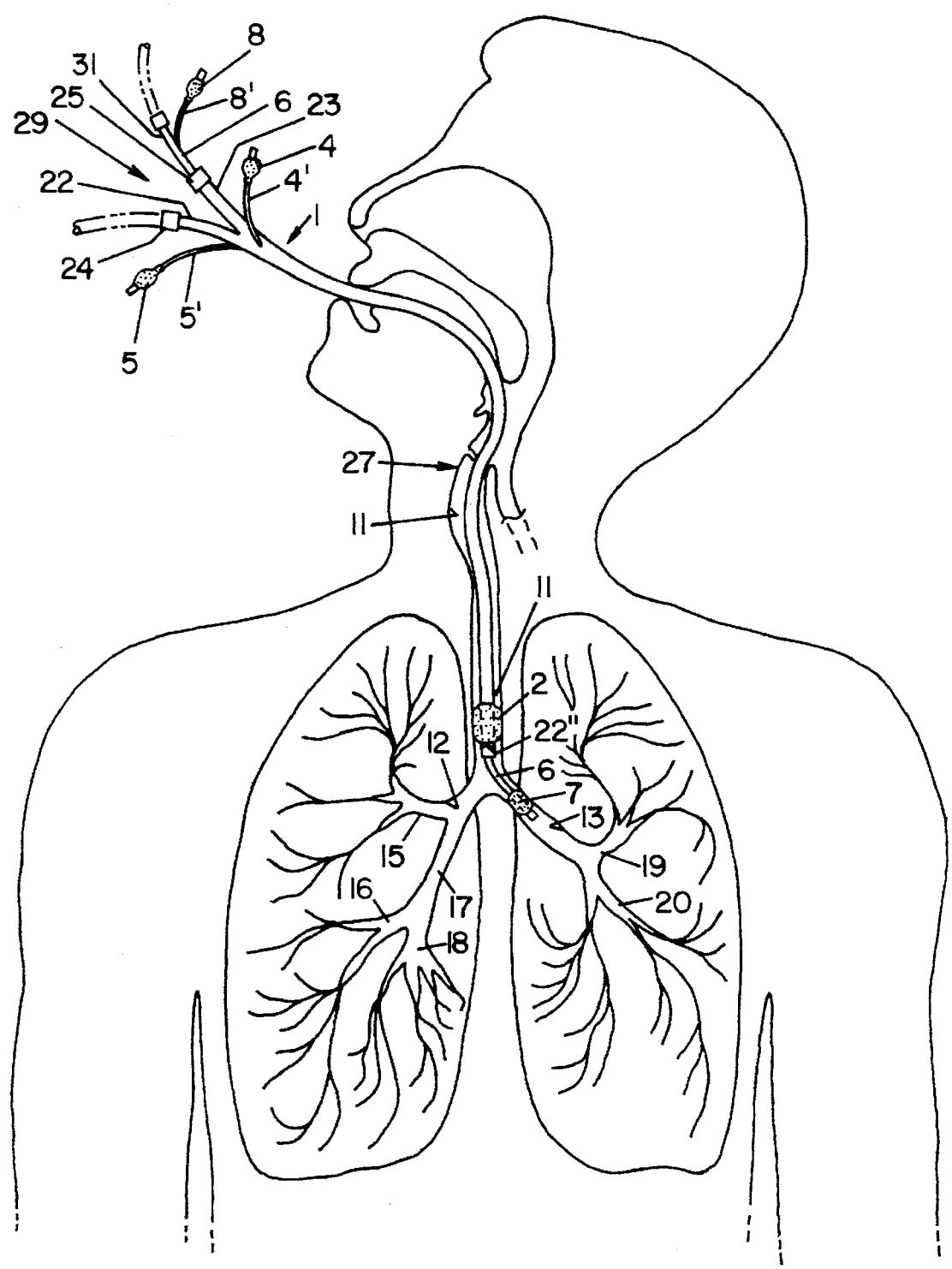
FIG. 1 is a genereally front schematic view of the invention positioned in a human being.

FIG. 1 is a generally front schematic view of the invention positioned in a human being. The common slave unit 1 is shown placed in the patient's mouth and trachea. The common slave unit 1 includes a proximal end portion 29, an intermediate portion 46 and a distal end portion 28 best seen in FIG. 2. The proximal end portion 29 resides generally outside of the patient. The intermediate portion and distal portions of the common slave unit extend into the trachea 11 of the patient. The trachea 11 is illustrated in FIG. 1.

FIG. 1 illustrates the trachea 11, the right main bronchus 12, and the left main bronchus 13. Also shown in FIG. 1 are the right upper lobe bronchus 15, the right intermediate bronchus 7, the right middle bronchus 16, and the right lower lobe bronchus 18. Similarly with respect to the left bronchus, the left upper lobe bronchus 19 and the left lower lobe bronchus 20 are shown. FIG. 1 also shows the glottis 27 of a human being.

Figure 2:
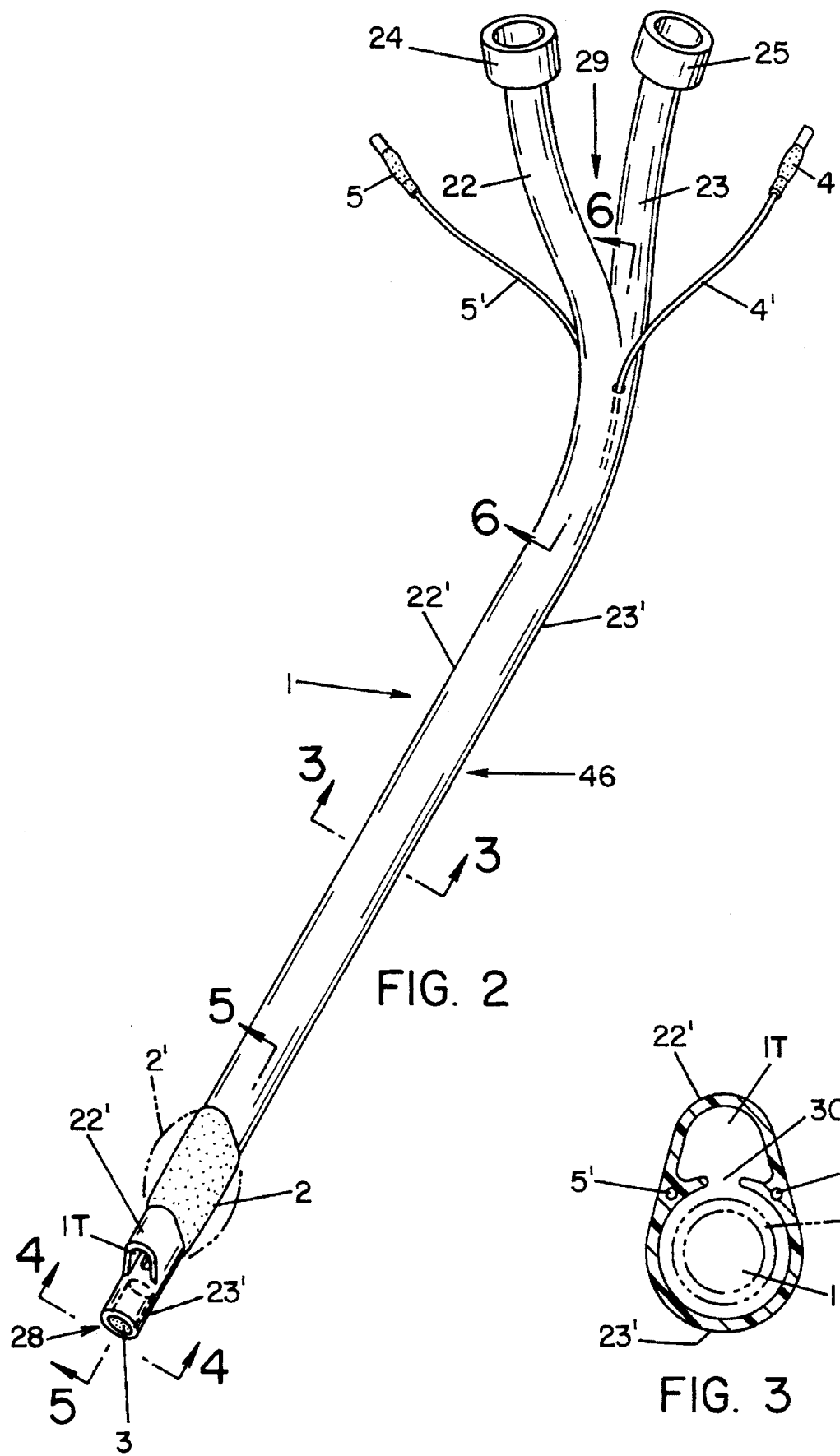
FIG. 2 is a perspective view of the common slave unit 1 illustrating the tracheal lumen 1T and the first inflatable cuff 2 and the second inflatable cuff 3.
Figure 6:
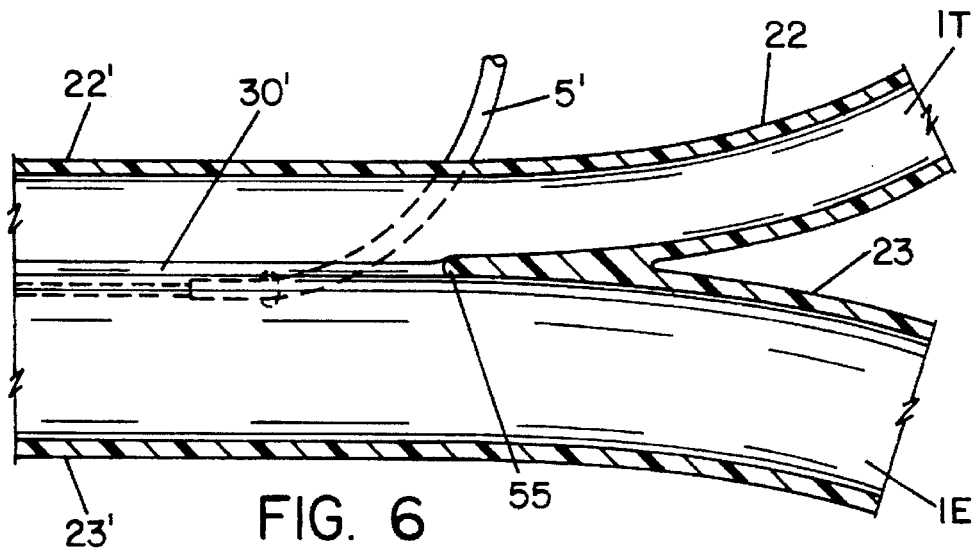
FIG. 6 is a cross-sectional view taken along the lines 6—6 of FIG. 1.

FIG. 2 shows in perspective view the common slave unit 1. The common slave unit has a tubular tracheal lumen 22 and a tubular endobronchial lumen 23 at the proximal end portion 29 thereof the tubular tracheal lumen 22 has a universal adaptor 24 for connection to other medical apparatus. Similarly the endobronchial lumen 23 has a universal adaptor 25 for connection to other medical apparatus. The tubular tracheal lumen 22 joins the tubular endobronchial lumen 23 as can be seen in FIG. 6. FIG. 6 is taken along the lines 6—6 of FIG. 2. FIG. 6 illustrates the joinder of the tracheal lumen 1T and the endobronchial lumen 1E. There exists a communicating passageway 30 between the tracheal lumen 1T and the endobronchial lumen 1E.

Figure 3:
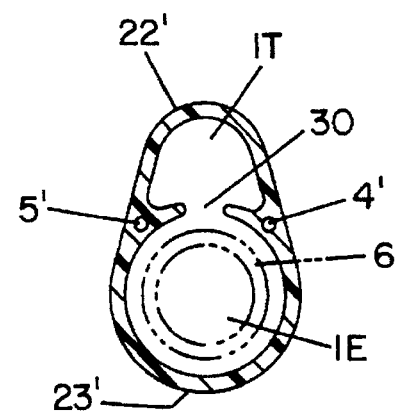
FIG. 3 is a sectional view of the common slave unit 1 illustrating the tracheal lumen 1T, the endobronchial lumen 1E, and the communicating passageway 30.

FIG. 3 is a cross-sectional view taken along the lines 3—3 of FIG. 2. FIG. 3 illustrates the communicating passageway 30 between the tracheal lumen 1T and the endobronchial lumen 1E. Additionally shown in FIG. 3 is the endobronchial tube 6 inserted into the endobronchial lumen 1E.

FIG. 2 shows an inflatable first cuff 2 residing about the common slave unit 1. The endobronchial cuff 2 is illustrated as being generally at the distal end portion 28 of the common slave unit 1. However, it will be understood to those skilled in the art that the first inflatable cuff 2 could be located in any one of a plurality of positions along the intermediate portion 46 of the common slave unit 1. The purpose of the first inflatable cuff 2 is to seal between the common slave unit 1 and the trachea 11 of a patient. See, FIG. 1. It will be noted from a review of FIG. 2 that a pump means 4 and a connecting means 4' lead from the proximal end portion 29 of the common slave unit 1 to the cuff 2. FIG. 3 illustrates the connecting means 4' in cross section. In the preferred embodiment the connecting means 4' is a simple duct and tube combination. In the preferred embodiment the pump means 4 is a bulb type air pump. These are known generally to those skilled in the art.

FIG. 2 further illustrates a second inflatable cuff, sometimes referred to herein as an inner cuff 3, at the distal end portion 28 of the common slave unit 1. It will be understood to those skilled in the art that the second inflatable cuff 3 need not necessarily be positioned at the distal end portion of the common slave unit 1 but may be placed in any one of a plurality of positions along the intermediate portion 46 of the common slave unit 1. The second inflatable cuff 3 may be positioned in the universal adaptor 25. FIG. 2 shows a pump means 5 and a connecting means 5' for inflating the second inflatable, cuff 3. In the preferred embodiment the pump means 5 is a bulb pump and the connecting means 5' is a tube and a passageway in the common slave unit 1. FIG. 3 shows the duct 5' in cross section.

FIG. 2 also illustrates that the tracheal lumen 1T resides generally and anteriorally with respect to the endobronchial lumen 1E. Reference numeral 22' is used to illustrate that the tracheal lumen 1T is generally oriented anteriorally with respect to the endobronchial lumen which is indicated by reference numeral 23'.

The inflatable cuffs 2 and 3 of the preferred embodiment are balloon type cuffs. Balloon type cuffs are known to those skilled in the art. Referring to FIG. 2, the reference numeral 2' illustrates the cuff 2 in its inflated condition.

Figure 4:
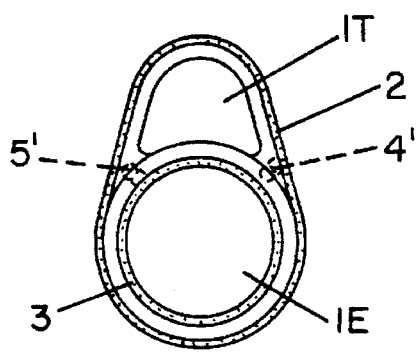
FIG. 4 is an end view of the common slave unit 1 illustrating the tracheal lumen 1T, the endobronchial lumen 1E, and the second inflatable cuff 3. Also shown is the passageway 5' in phantom which supplies air to the inflatable balloon 3.

FIG. 4 is an end view of the common slave unit 1 taken along the lines 4—4 of FIG. 2. FIG. 4 illustrates the interconnection of the passageway 5' and the inflatable balloon cuff 3, also known as the second inflatable cuff. FIG. 4 also illustrates in phantom the duct 4' which leads to the inflatable cuff 2 the inflatable cuff 2 is also shown in FIG. 4.

Figure 5:
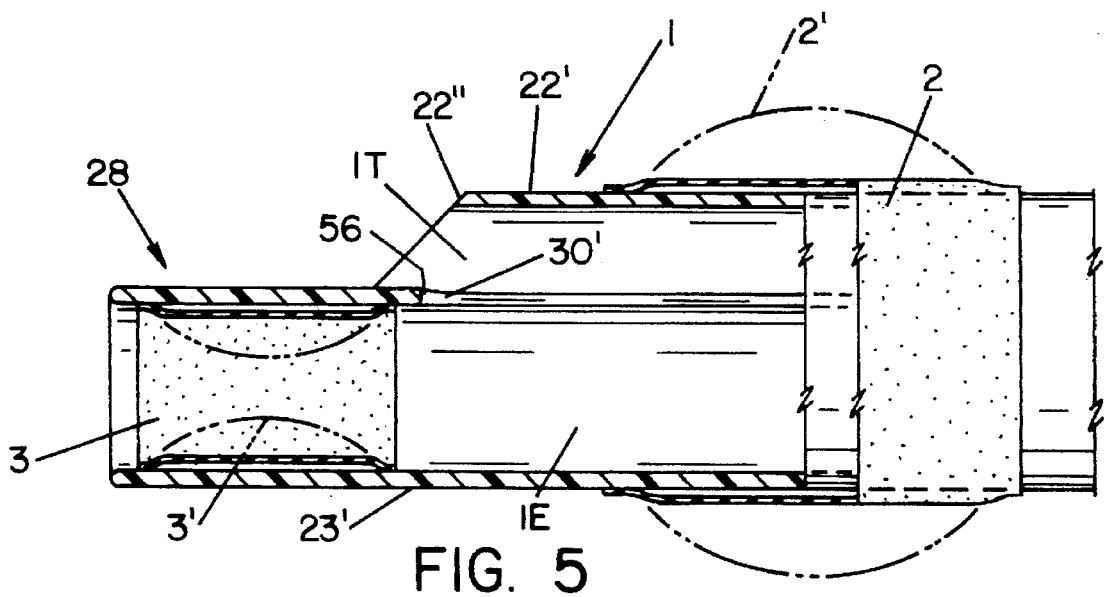
FIG. 5 is a sectional view taken along the lines 5—5 of FIG. 1.

FIG. 5 is taken along the line 5—5 of FIG. 2 and is a semi-cross-sectional view of the distal end portion 28 of the common slave unit 1. The inflatable cuffs 2 and 3 are shown in FIG. 5. The inflatable cuff 3 is shown in its expanded state or position by the broken line which is denoted by reference numeral 3'. The inflatable cuff 2 is shown in its expanded or enlarged position by the broken line noted by reference numeral 2'. FIG. 5 also shows the tracheal lumen 1T and the endobronchial lumen 1E. FIG. 5 also shows a beveled leading edge 22" of the tracheal lumen 1T. FIG. 6 shows the tracheal lumen 1T and the endobronchial lumen 1E. The tracheal lumen 1T is joined with the endobronchial lumen 1E at a point designated by reference numeral 55 in FIG. 6. Slot 30 shown in FIG. 3 communicates between the tracheal lumen 1T and the endobronchial lumen 1E from the point 55 shown in FIG. 6 to the point 56 shown in FIG. 5. This slot ms formed by wall means 30'. Slot 30 provides for increased flexibility of common slave unit 1 and provides for increased air flow through the common slave unit.

The common slave unit and the endobronchial tubes are manufactured from any one of a number of soft plastic materials. These materials are typically polyvinyl chloride or similar synthetic materials.

FIG. 7 illustrates a perspective view of the left endobronchial tube 6 preformed for left curvature for insertion into the left bronchus. FIG. 7 illustrates the left endobronchial tube 6 having a proximal end portion 31 and a distal end portion 32. The proximal end portion 31 is also seen in FIG. 1. FIG. 7 also shows a pump means 8 and a means to connect the pump 8' with a third inflatable cuff 7. The third inflatable cuff 7 is sometimes referred to herein as the endobronchial cuff.

FIG. 8 is a cross-sectional view of the left endobronchial tube 6 taken along the lines 8—8 of FIG. 7. FIG. 8 illustrates the passageway 8'. The passageway 8' leads from the pump 8 to the inflatable cuff 7.

FIG. 9 is taken along the lines 9—9 of FIG. 7. FIG. 9 illustrates the inflatable cuff 7 as well as the passageway or duct 8' leading to the inflatable cuff 7. Reference numeral 7' is used in FIG. 9 to illustrate the approximate position that the inflatable balloon type cuff 7 will assume once inflated.

FIG. 1 illustrates the positioning of the left endobronchial tube 6 in the left main bronchus 13. FIG. 1 illustrates the inflatable cuff 7 having been expanded to secure and seal the endobronchial tube 6 with respect to the left main bronchus 13. At the proximal end portion 29 of the common slave unit, the endobronchial tube 6 is illustrated as extending beyond the proximal end portion 29 of the common slave unit 1.

FIG. 10 illustrates the preferred embodiment of the right endobronchial tube 36 preformed for right curvature for positioning into the right bronchus. FIG. 10 illustrates two inflatable cuffs 38 and 39. FIG. 10 also illustrates a pathway 45 therethrough. FIG. 10 illustrates an inflatable pump means 37 and an interconnecting tube 37' which interconnects the pump means 37 and the inflatable cuffs 38 and 39.

FIG. 11 is a cross-section view of a portion of FIG. 10 taken along the lines 11—11. FIG. 11 illustrates the passageway 37' interconnecting to the inflatable cuffs 38 and 39. Reference numerals 38' and 39' illustrate the expansion of the inflatable cuffs when they are pressurized.

FIG. 10A is another embodiment of the endobronchial tube. In FIG. 10A the endobronchial tube is represented by the numeral 40. The embodiment shown in FIG. 10A has a pump means 42 and interconnecting means 42' and an inflatable cuff 41. The interconnecting means 42' connects the pump and the inflatable cuff 41 in the exact same manner illustrated in FIG. 10. FIG. 10A illustrates opening 44 for ventilating the right lung of a patient. FIG. 10A is an embodiment for use with the right lung of the patient and endobronchial tube 40 as shown in FIG. 10A has right preformed curvature.

Figure 12A:
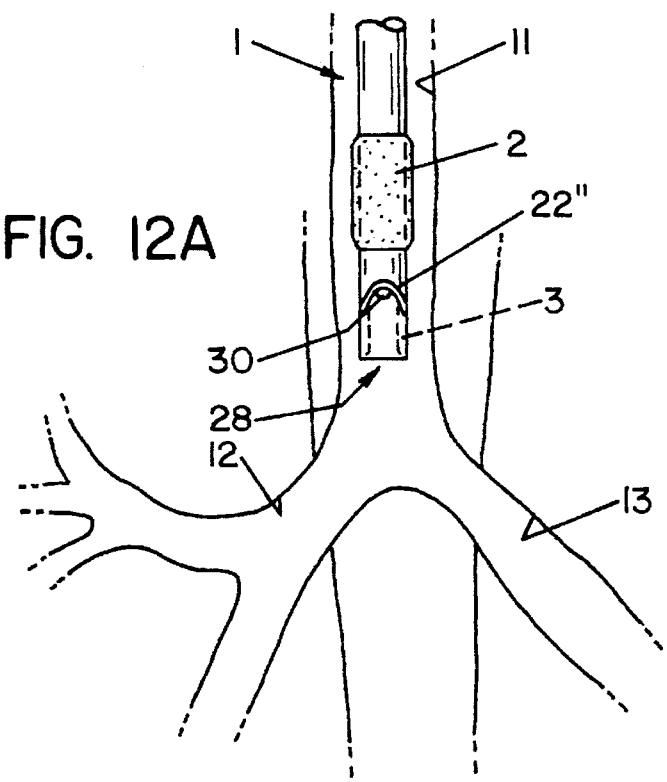
FIG. 12A illustrates the insertion and positioning of the common slave unit in the trachea of a human being. Cuff 2 is shown not inflated.

FIG. 12A illustrates the insertion of the common slave unit 1 into the trachea of a human being. Also shown in FIG. 12A are the trachea 11, the first inflatable cuff 2 surrounding the common slave unit 1, the left main bronchus 13 and the right main bronchus 12. The distal end portion 28 of the common slave unit is illustrated in FIG. 12A. The interconnecting slot between the tracheal lumen 1T and the endobronchial lumen 1E is shown and designated by reference numeral 30. The second inflatable cuff 3 is shown in phantom. The beveled leading edge 22' of the tracheal lumen is also shown in FIG. 12A. The beveled leading edge 22' of the tracheal lumen serves to aid in the insertion of the common slave unit into the patient.

Figure 12B:
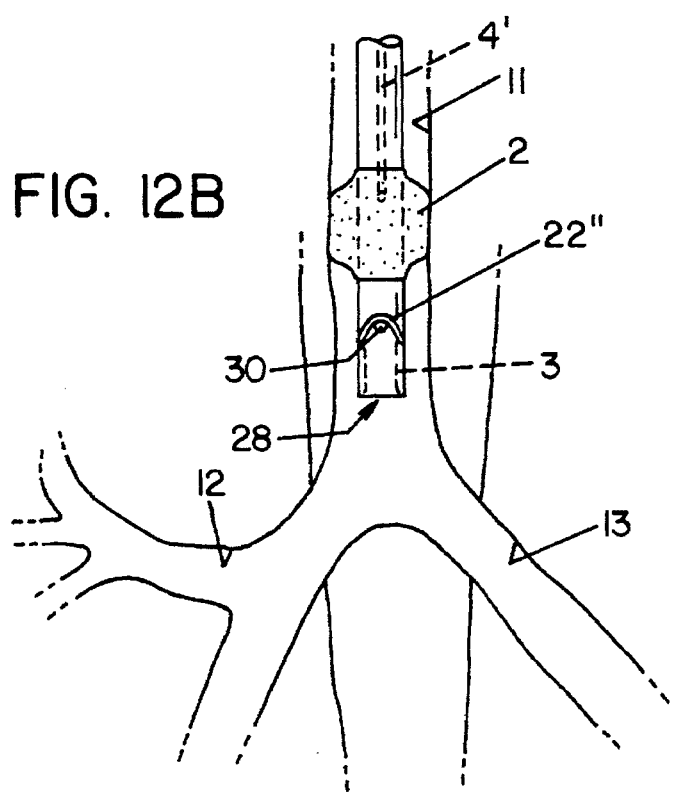
FIG. 12B illustrates the insertion and positioning of the common slave unit in the trachea of a human being. Cuff 2 is shown inflated.

FIG. 12B is similar to FIG. 12A except that additionally the first inflatable cuff 2 is shown inflated. This has the effect of stabilizing and sealing the common slave unit with respect to the trachea 11. The duct leading from pump means 4 to the inflatable cuff 2 is shown in phantom by reference numeral 4'. Once the first inflatable cuff 2 is inflated, it seals and prevents any fluid from exiting the patient by means of the trach. Of course, the tracheal lumen and the endobronchial lumen permit, under controlled circumstances, fluids and gasses to enter and exit as desired from either or both the left main bronchus or the right main bronchus.

Figure 12C:
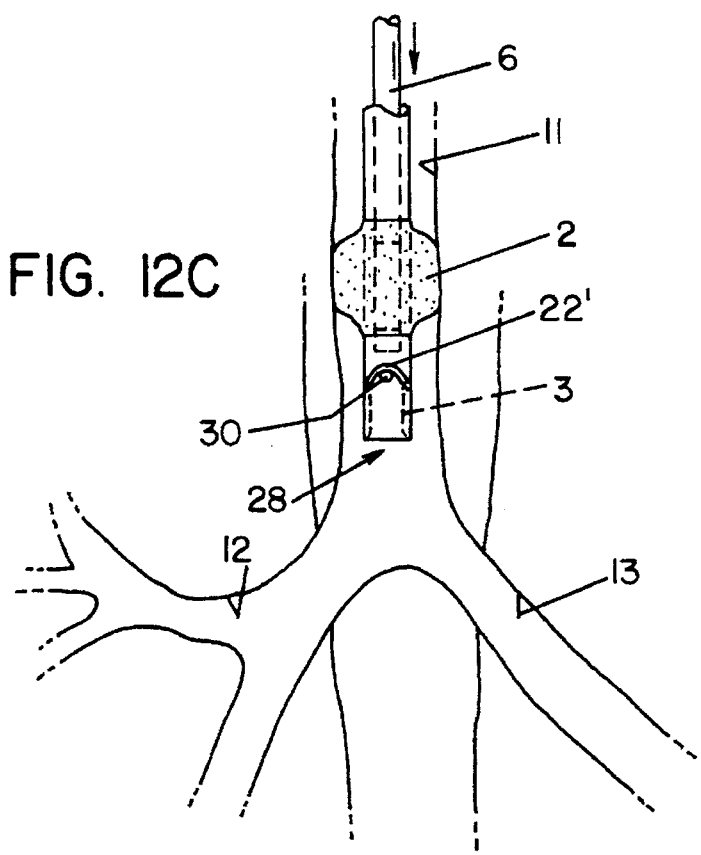
FIG. 12C illustrates the view similar to that as shown in FIG. 2B.

FIG. 12C illustrates the endobronchial tube 6 being inserted into and through the endobronchial lumen 1E of the common slave unit 1.

Figure 12D:
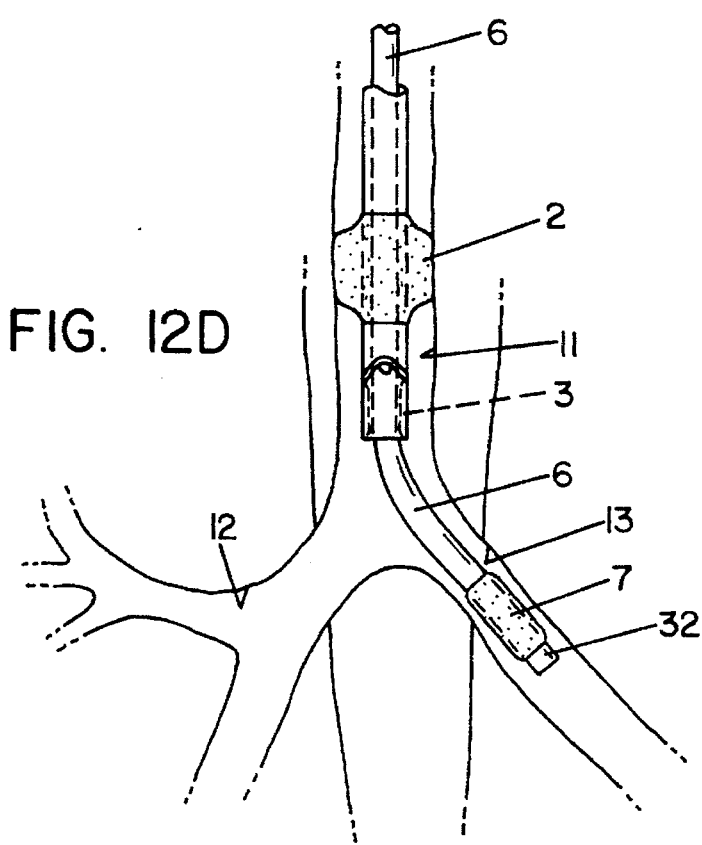
FIG. 12D illustrates the full insertion of the endobronchial tube 6 in the left main bronchus.

FIG. 12D illustrates the endobronchial lumen 6 positioned in the left main bronchus 13.

Figure 12E:
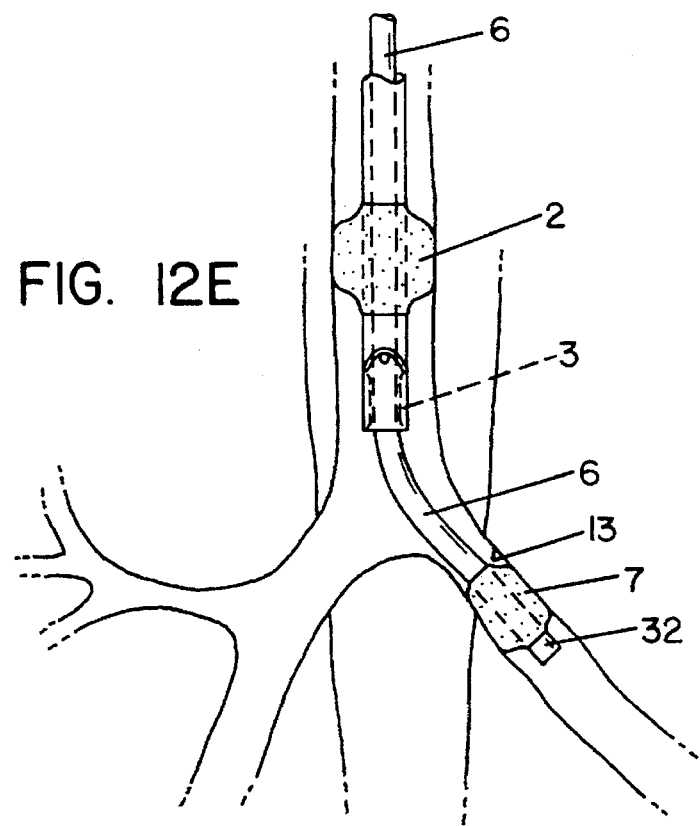
FIG. 12E illustrates the full insertion of the endobronchial tube 6 in the left main bronchus with the endobronchial cuff 7, sometimes referred to as the third inflatable cuff, inflated.

FIG. 12E illustrates the third inflatable cuff 7, also known as the endobronchial cuff 7, inflated and sealing and securing the endobronchial tube 6 with respect to the left main bronchus.

Figure 12F:
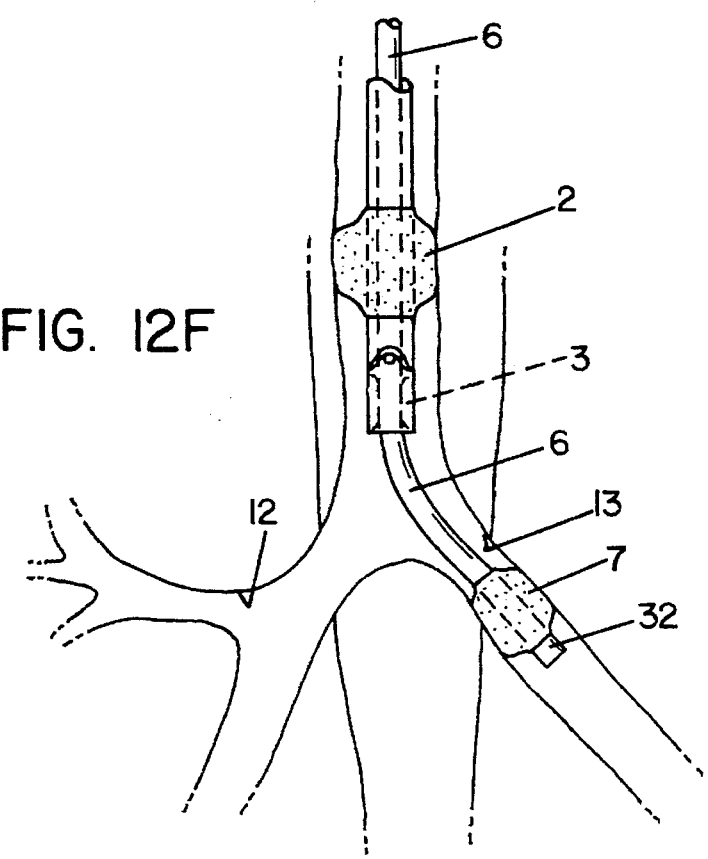
FIG. 12F illustrates the view similar to that of FIG. 12E.

FIG. 12F shows the second inflatable cuff 3 inflated securing and sealing the left endobronchial tube 6 with respect to the common slave unit. This second inflatable cuff 3 secures and stabilizes the endobronchial tube 6 with respect to the common slave unit 1.

Figure 13A:
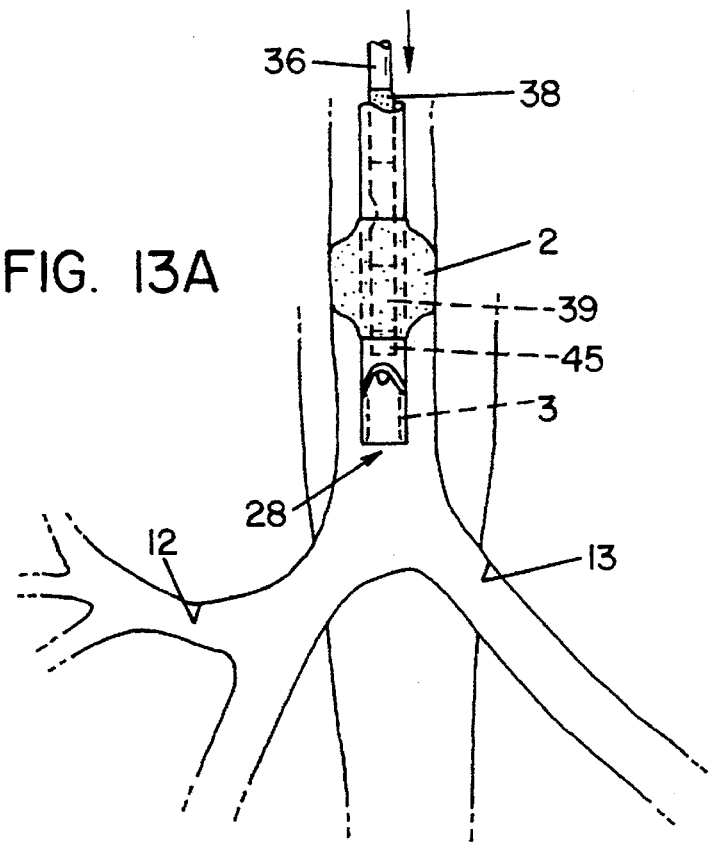
FIG. 13A illustrates the common slave unit residing within the trachea of a patient.
Figure 13B:
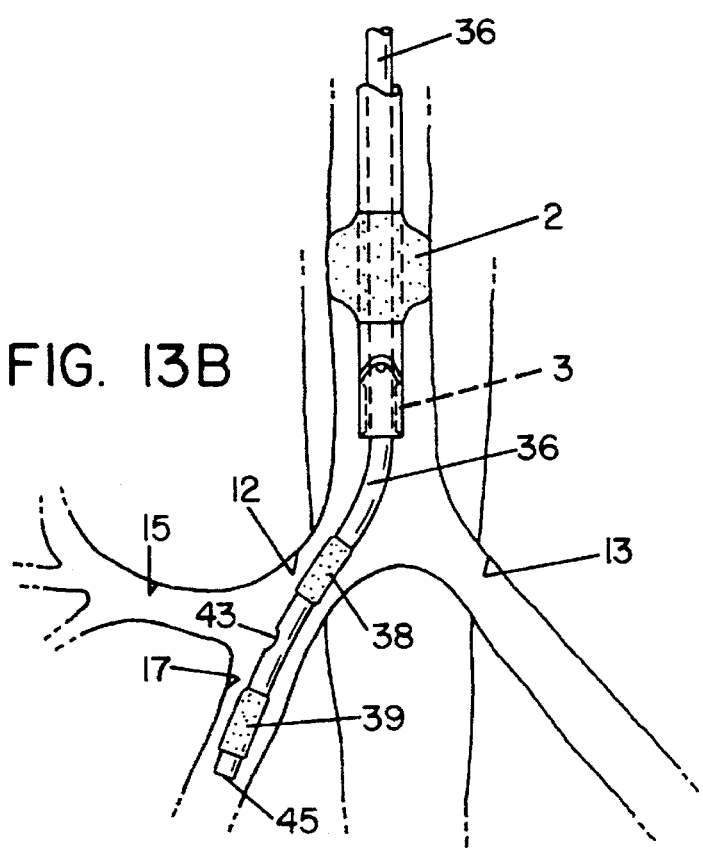
FIG. 13B illustrates the endobronchial tube 36 positioned in the right main and intermediate bronchus.

FIG. 13A is similar to FIG. 12C. FIG. 13A illustrates the insertion of right endobronchial tube 36 through the endobronchial lumen 1E of the common slave unit 1. FIG. 13B illustrates the positioning of the right endobronchial tube 36 with respect to the right main bronchus and the right intermediate bronchus. The aperture 43 is positioned to allow medication and anesthesia to flow freely into the right upper lobe bronchus 15. The opening 45 is positioned to allow medication and anesthesia to flow freely into the right lower lobe bronchus 18. The pathways for the flow are the aperture 43 and the opening 45 shown in FIG. 13B.

Figure 13C:
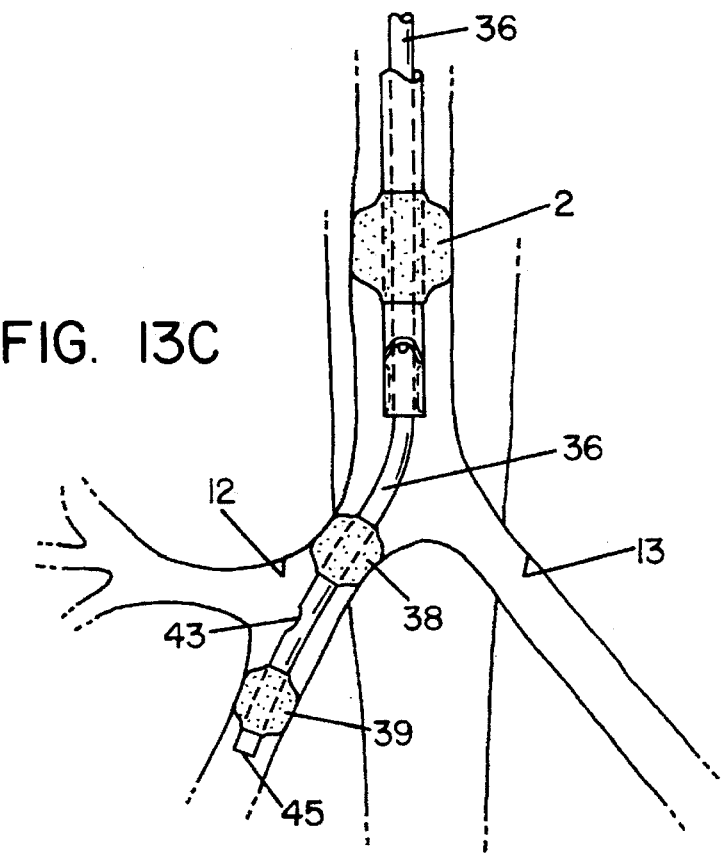
FIG. 13C illustrates the endobronchial tube positioned as shown i n FIG. 13B together with the third and fourth cuffs inflated. The third and fourth cuffs are both endobronchial cuffs.

FIG. 13C illustrates bronchial cuffs 38 and 39 inflated sealing and positioning the right endobronchial tube 36 with respect to the right bronchus.

Figure 13D:
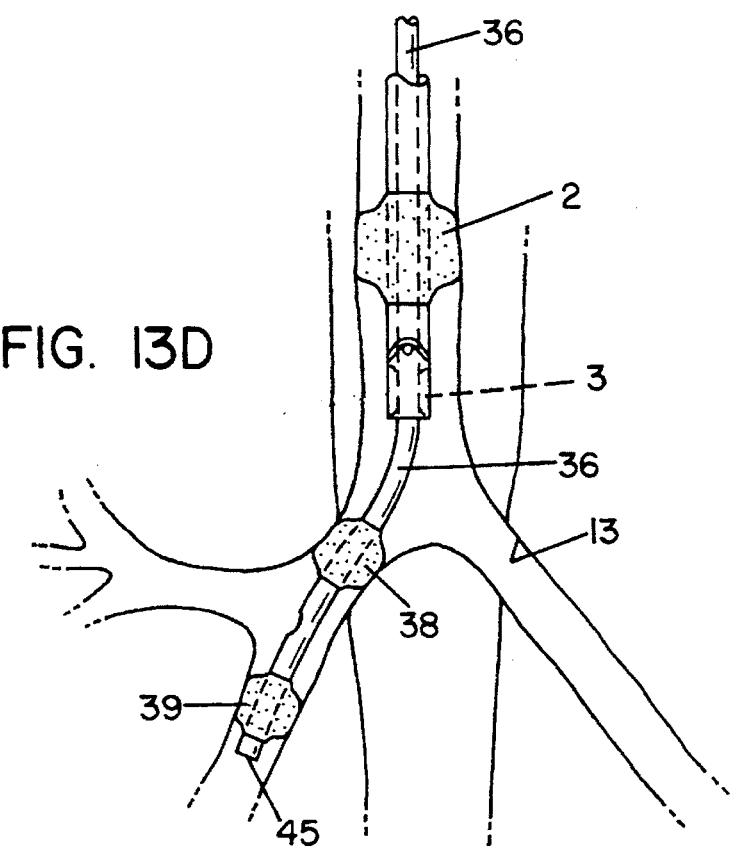
FIG. 13D is similar to FIG. 13C.

FIG. 13D illustrates the second inflatable cuff 3 engaging the right endobronchial tube 36. Reference numeral 42 indicates the second inflatable cuff 3 gripping and engaging the right endobronchial tube 36.

It will be note to those skilled in the art that the endobronchial tubes and the common slave unit will be of various lengths depending on the size of the patient. The endobronchial tube have sufficient flexibility such that the left preformed curvature and the right preformed curvature for the respective endobronchial tubes can be easily inserted through the endobronchial tube 1E of the common slave unit.

It will be understood by those skilled in the art that the method of use of the invention disclosed herein will be generally as follows. The common slave unit 1 is first placed in the patient's trachea. After the common slave unit is placed in the patient's trachea, the tracheal cuff 2, also known as the first inflatable cuff 2, will be inflated. Once the tracheal cuff 2 is inflated, a seal is effected between the outside of the common slave unit and the trachea. The patient will then be ventilate, and the lungs ausculates to confirm equal air in both lungs. Next either the left endobronchial tube or the right endobronchial tube will be positioned in the patient. Once the left endobronchial tube or the right endobronchial tube is placed in the patient, one or more of the endobronchial cuffs will then be inflated to seal the respective bronchus. Once the endobronchial tube is positioned and sealed the inner cuff 3, referred to herein as the second inflatable cuff will be inflated to prohibit movement and/or dislodgment of the endobronchial tube with respect to the common slave unit and with respect to the bronchus. The position of the endobronchial tubes in their respective lungs will be confirmed by selective ventilation or by fiberoptic bronchoscope procedures.

The invention has been described in detail with particular emphasis on the preferred embodiments thereof, but it should be understood that variations and modifications within the spirit and scope of the invention may occur to those skilled in the art to which the invention pertains.

Other methods of use will be readily apparent to those skilled the art.

What is claimed is:

1. An endotracheal device comprising a common slave unit and an endobronchial tube, said common slave unit includes a tracheal lumen and an endobronchial lumen, a first inflatable cuff, said first inflatable cuff resides around a section of said common slave unit and expands radially outwardly sealing against the trachea of a human being and said common slave unit, said endobronchial tube partially resides in said endobronchial lumen of said common slave unit and extends through said endobronchial lumen into a main bronchus of a human being, a second inflatable cuff, said second inflatable cuff resides annularly within said endobronchial lumen of said common slave unit and expands radially inwardly sealing against said endobronchial tube and said endobronchial lumen, a third inflatable cuff, and, said third inflatable cuff resides around a section of said endobronchial tube and expands radially outwardly sealing against said main bronchus of a human being and said endobronchial tube.

2. An endotracheal device as claimed in claim 1 wherein said endobronchial lumen of said common slave unit communicates with said tracheal lumen of said common slave unit.

3. An endotracheal device as claimed in claim 1 wherein said tracheal lumen of said common slave unit is oriented generally anteriorly and said endobronchial lumen is oriented generally posteriorly.

4. An endotracheal device as claimed in claim 3 wherein said first inflatable cuff, said second inflatable cuff, and said third inflatable cuff are balloon type cuffs.

5. An endotracheal device as claimed in claim 1 wherein said endobronchial tube includes a preformed left curvature.

6. An endotracheal device as claimed in claim 1 wherein said endobronchial tube includes a preformed right curvature.

7. An endotracheal device as claimed in claim 6 wherein said third inflatable cuff seals against the right main bronchus and wherein said endotracheal device further includes a fourth inflatable cuff, said fourth inflatable cuff resides around a section of said endobronchial tube and expands radially outwardly sealing against the right intermediate bronchus of a human being.

8. An endotracheal device as claimed in claim 7 wherein said endobronchial tube includes an aperture located intermediate said third and fourth inflatable cuffs.

9. An endotracheal device as claimed in claim 5 wherein said endobronchial tube is generally cylindrically shaped.

10. An endotracheal device as claimed in claim 6 wherein said endobronchial tube is generally cylindrically shaped.

11. An endotracheal device as claimed in claim 8 wherein said endobronchial tube is generally cylindrically shaped.

12. An endotracheal device comprising a common slave unit, said common slave unit includes a proximal end portion, an intermediate portion, and a distal end portion, said proximal end portion includes a tubular tracheal lumen and a tubular endobronchial lumen, said tubular tracheal lumen and said tubular endobronchial lumen being joined together distally forming a glottis shaped intermediate portion, said intermediate portion having a tracheal lumen communicating with an endobronchial lumen, said tracheal lumen extending to said distal end portion of said common slave unit and terminates in a beveled edge at said distal end portion, said endobronchial lumen terminates at said distal end portion of said common slave unit, a first inflatable cuff securing and sealing said common slave unit with respect to the trachea of a human being, an endobronchial tube, said endobronchial tube resides partially within said tubular endobronchial lumen and said endobronchial lumen of said intermediate portion, said endobronchial tube extending proximally from said tubular endobronchial lumen of said proximal end portion of said common slave unit, said endobronchial tube extending distally from said endobronchial lumen of said distal end portion of said common slave unit and into a main bronchus of a human being, a second inflatable cuff securing and sealing said endobronchial tube with respect to said endobronchial lumen of said common slave unit, a third inflatable cuff resides around a distal section of said endobronchial tube and secures and seals said endobronchial tube with respect to said main bronchus.

13. An endotracheal device as claimed in claim 12 wherein said endobronchial tube is preformed for insertion into the left main bronchus.

14. An endotracheal device as claimed in claim 12 wherein said endobronchial tube is preformed for insertion into the right main bronchus.

15. An endotracheal device as claimed in claim 12 wherein said first inflatable cuff, said second inflatable cuff, and said third inflatable cuff are balloon type cuffs.

16. An endotracheal device as claimed in claim 12 wherein said third inflatable cuff seals against the right main bronchus and wherein said endotracheal device further includes a fourth inflatable cuff, said fourth inflatable cuff resides around a section of said endobronchial tube and expands radially outwardly sealing against the right intermediate bronchus of a human being.

17. An endotracheal device as claimed in claim 16 wherein said endobronchial tube includes an aperture located intermediate said third and fourth inflatable cuffs.

* * * * *

UNITED STATES PATENT AND TRADEMARK OFFICE
CERTIFICATE OF CORRECTION

PATENT NO. : 5,660,175
DATED : August 26, 1997
INVENTOR(S) : Bimal Dayal

It is certified that error appears in the above-indentified patent and that said Letters Patent is hereby corrected as shown below:

Col. 1, line 59, delete "lockers" and insert -- blockers --.

Col. 1, line 65, after "with", insert -- a --.

Col. 2, line 26, delete "ms" and insert -- is --.

Col. 4, line 41, delete "2B" and insert -- 12B --.

Col. 5, line 20, delete "7", and insert --17 --.

Col. 5, line 28, delete "thereof the" and insert -- thereof. The --

Col. 6, line 39, delete "ms" and insert -- is --.

Col. 7, line 49, delete "trach" and insert -- trachea --.

Col. 8, line 19, delete "note" and insert -- noted --.

UNITED STATES PATENT AND TRADEMARK OFFICE
CERTIFICATE OF CORRECTION

PATENT NO. : 5,660,175
DATED : August 26, 1997
INVENTOR(S) : Bimal Dayal

It is certified that error appears in the above-indentified patent and that said Letters Patent is hereby corrected as shown below:

Col. 8, line 22, delete "tube" and insert -- tubes --.

Col. 8, line 36, delete "ausculates" and insert -- auscultated --.

Signed and Sealed this

Twenty-first Day of October 1997

BRUCE LEHMAN

Attest:

Attesting Officer

Commissioner of Patents and Trademarks